(12) United States Patent
Yacoby et al.

(10) Patent No.: US 10,369,033 B2
(45) Date of Patent: Aug. 6, 2019

(54) DELIVERY SYSTEM AND METHOD OF USE FOR DEPLOYMENT OF SELF-EXPANDABLE VASCULAR DEVICE

(71) Applicant: MERIT MEDICAL IRELAND LIMITED, Dublin (IE)

(72) Inventors: Menashe Yacoby, Shoham (IL); Ascher Shmulewitz, Tel Aviv (IL); Raz Bar-On, Moshav Tel Adashim (IL); Gil Naor, Ramat-Hasharon (IL); Damian Kelly, Galway (IE); Michael Gilmore, Galway (IE); Mark Steckel, Sharon, MA (US)

(73) Assignee: MERIT MEDICAL IRELAND LIMITED, Dublin (IE)

( * ) Notice: Subject to any disclaimer, the term of this patent is extended or adjusted under 35 U.S.C. 154(b) by 507 days.

(21) Appl. No.: 14/971,630

(22) Filed: Dec. 16, 2015

(65) Prior Publication Data
US 2016/0166416 A1    Jun. 16, 2016

Related U.S. Application Data

(63) Continuation of application No. 14/643,474, filed on Mar. 10, 2015, now abandoned, which is a
(Continued)

(51) Int. Cl.
| | |
|---|---|
| *A61F 2/97* | (2013.01) |
| *A61F 2/88* | (2006.01) |
| *A61F 2/91* | (2013.01) |
| *A61F 2/915* | (2013.01) |

(Continued)

(52) U.S. Cl.
CPC ............... *A61F 2/97* (2013.01); *A61F 2/844* (2013.01); *A61F 2/88* (2013.01); *A61F 2/91* (2013.01);
(Continued)

(58) Field of Classification Search
CPC .. A61F 2/97; A61F 2/844; A61F 2/958; A61F 2002/9522; A61F 2/88;
(Continued)

(56) References Cited

U.S. PATENT DOCUMENTS

| | | | |
|---|---|---|---|
| 4,950,227 A | 8/1990 | Savin et al. | |
| 5,403,341 A | 4/1995 | Solar | |

(Continued)

FOREIGN PATENT DOCUMENTS

| | | |
|---|---|---|
| EP | 0 876 802 A2 | 11/1998 |
| WO | 01/97715 A1 | 12/2001 |

OTHER PUBLICATIONS

Nov. 21, 2017 Office Action issued in U.S. Appl. No. 14/643,474.
(Continued)

*Primary Examiner* — David C Eastwood
*Assistant Examiner* — Erich Herbermann
(74) *Attorney, Agent, or Firm* — Oliff PLC

(57) ABSTRACT

A delivery system that includes a catheter, a balloon, a self-expanding prosthesis, and a sheath. The sheath including an opening in a wall of the sheath that initiates rupturing of the sheath so that the self-expanding prosthesis may move from its compressed state to its expanded state. Additionally, a distal end portion of the balloon that is distal to a distal end of the sheath includes an enlarged diameter portion, the enlarged diameter portion having approximately the same outer diameter as an outer diameter of the sheath when the self-expanding prosthesis is in its compressed state, and the enlarged diameter portion being the maximum outer diameter of the balloon when the self-expanding prosthesis is in its compressed state.

11 Claims, 18 Drawing Sheets

Related U.S. Application Data continuation of application No. 11/457,621, filed on Jul. 14, 2006, now abandoned.

(60) Provisional application No. 60/699,151, filed on Jul. 14, 2005.

(51) Int. Cl.

| | |
|---|---|
| *A61F 2/958* | (2013.01) |
| *A61F 2/966* | (2013.01) |
| *A61M 25/10* | (2013.01) |
| *A61F 2/844* | (2013.01) |
| *A61F 2/82* | (2013.01) |
| *A61F 2/95* | (2013.01) |

(52) U.S. Cl.
CPC .............. *A61F 2/915* (2013.01); *A61F 2/958* (2013.01); *A61F 2/966* (2013.01); *A61M 25/10* (2013.01); *A61M 25/1034* (2013.01); A61F 2002/821 (2013.01); A61F 2002/91525 (2013.01); A61F 2002/91533 (2013.01); A61F 2002/91558 (2013.01); A61F 2002/9522 (2013.01); A61F 2002/9583 (2013.01); A61F 2230/005 (2013.01); A61F 2230/0054 (2013.01); A61F 2250/0039 (2013.01); A61M 2025/1081 (2013.01); Y10T 29/4987 (2015.01)

(58) Field of Classification Search
CPC .. A61F 2/966; A61F 2/91; A61F 2/915; A61F 2002/9583; A61M 25/1034; A61M 25/10; A61M 2/915; A61M 2025/1081
See application file for complete search history.

(56) References Cited

U.S. PATENT DOCUMENTS

| | | | |
|---|---|---|---|
| 5,549,635 | A | 8/1996 | Solar |
| 5,549,663 | A | 8/1996 | Cottone, Jr. |
| 5,632,762 | A | 5/1997 | Myler |
| 5,980,530 | A | 11/1999 | Willard et al. |
| 6,497,722 | B1 | 12/2002 | Von Oepen et al. |
| 6,544,218 | B1 | 4/2003 | Choi |
| 6,656,213 | B2 | 12/2003 | Solem |
| 9,345,602 | B2 * | 5/2016 | Ngo ................. A61F 2/915 |
| 2002/0072789 | A1 | 6/2002 | Hackett et al. |
| 2003/0040790 | A1 | 2/2003 | Furst |
| 2003/0065376 | A1 | 4/2003 | Seppala et al. |
| 2003/0069561 | A1 | 4/2003 | Choi |
| 2004/0015224 | A1 | 1/2004 | Armstrong et al. |
| 2004/0093058 | A1 | 5/2004 | Cottone et al. |
| 2004/0148000 | A1 | 7/2004 | Bilge |
| 2005/0228483 | A1 | 10/2005 | Kaplan et al. |
| 2006/0015171 | A1 * | 1/2006 | Armstrong ....... A61B 17/12022 623/1.12 |
| 2006/0184226 | A1 | 8/2006 | Austin |
| 2007/0260302 | A1 | 11/2007 | Igaki |

OTHER PUBLICATIONS

Mar. 25, 2016 Office Action Issued in U.S. Appl. No. 14/643,474.
Nov. 2, 2006 International Search Report issued in PCT/US2006/027375.
Nov. 2, 2016 Office Action issued in U.S. Appl. No. 14/643,474.

\* cited by examiner

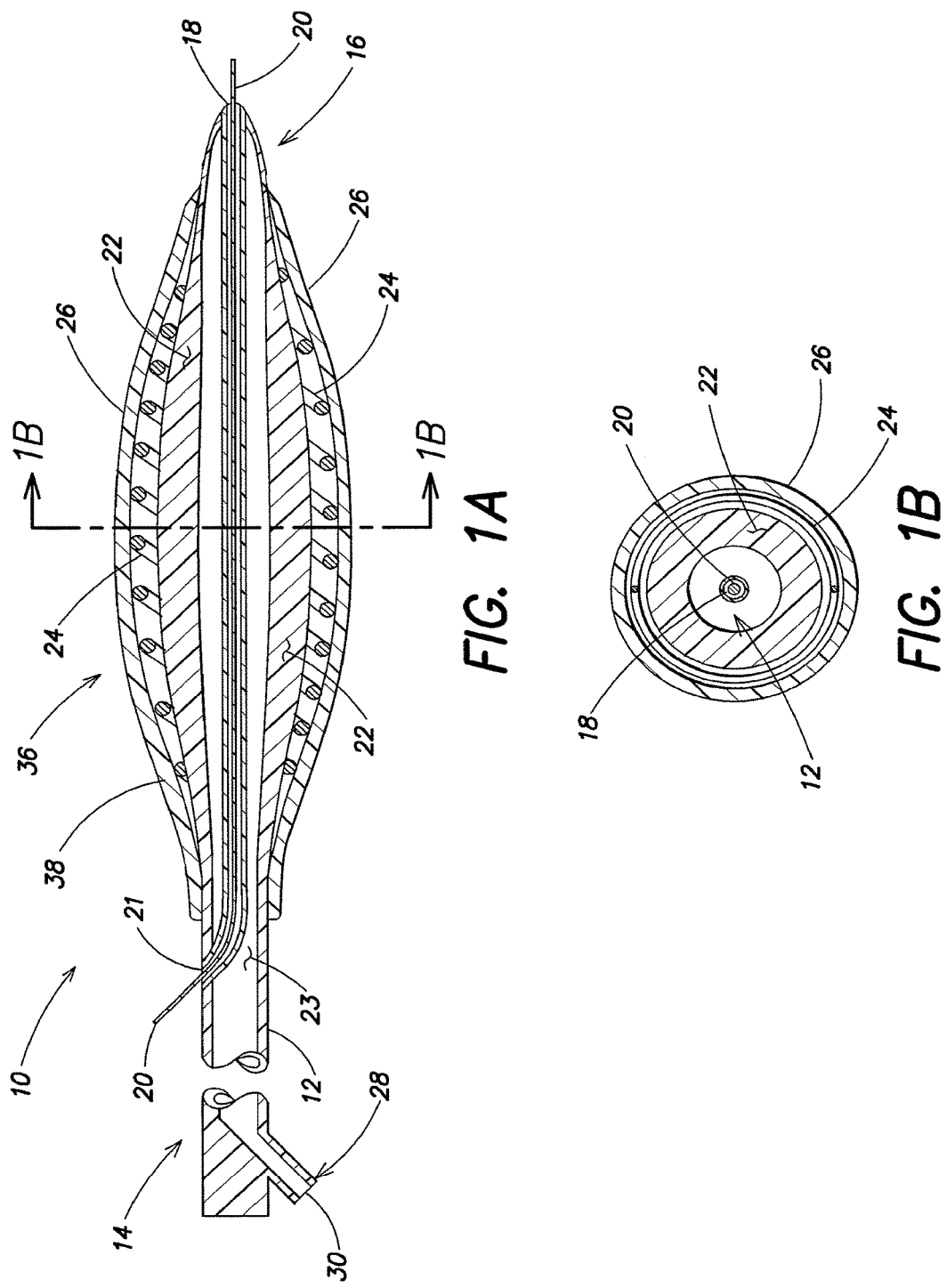

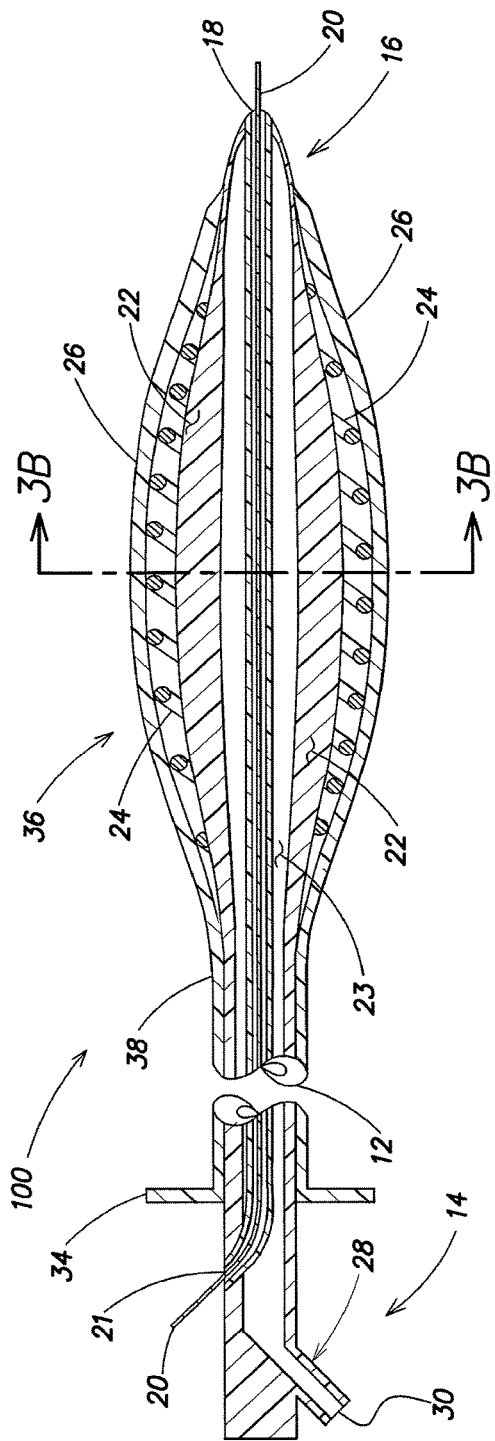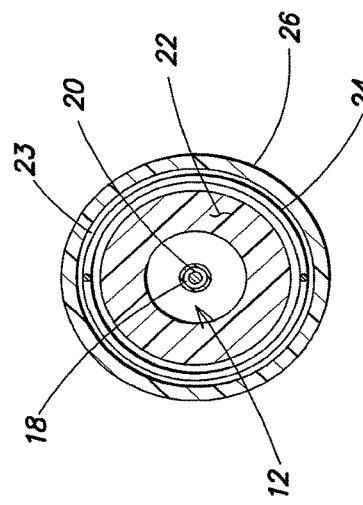
FIG. 3A
FIG. 3B

//DELIVERY SYSTEM AND METHOD OF USE FOR DEPLOYMENT OF SELF-EXPANDABLE VASCULAR DEVICE

RELATED APPLICATIONS

This application is a continuation of U.S. application Ser. No. 14/643,474, filed Mar. 10, 2015, which claims priority to U.S. application Ser. No. 11/457,621, filed Jul. 14, 2006, which claims priority to U.S. Provisional Patent Application No. 60/699,151, filed Jul. 14, 2005, the entire contents of which are hereby incorporated by reference.

TECHNICAL FIELD

The present disclosure relates to a delivery system and method for deployment of a vascular device and, more particularly, to a delivery system and method for deployment of a self-expanding vascular device.

BACKGROUND

Tubular prostheses typically fall into two general categories of construction. The first category of prosthesis is expandable upon application of a controlled force, often through the inflation of the balloon portion of a dilatation catheter, which expands the compressed prosthesis to a larger diameter to be left in place within a vessel, e.g., an artery, at the target site. The second category of prosthesis is a self-expanding prosthesis formed from, for example, shape memory metals or super-elastic Nickel-Titanium (NiTi) alloys, that will automatically expand from a compressed state when the prosthesis is advanced out of the distal end of the delivery catheter into the blood vessel.

Some known prosthesis delivery systems for implanting self-expanding stents include an inner lumen upon which the compressed or collapsed prosthesis is mounted and an outer restraining sheath that is initially placed over the compressed prosthesis prior to deployment. When the prosthesis is to be deployed in the body vessel, the outer sheath is moved in relation to the inner lumen to "uncover" the compressed prosthesis, allowing the prosthesis to move to its expanded condition. Some delivery systems utilize a "push-pull" design and technique in which the outer sheath is retracted while the inner lumen is pushed forward. Still other systems use an actuating wire that is attached to the outer sheath. When the actuating wire is pulled to retract the outer sheath and deploy the prosthesis, the inner lumen must remain stationary, to prevent the prosthesis from moving axially within the body vessel.

There have been, however, problems associated with these delivery systems. Systems that use the "push-pull" design can experience movement of the collapsed prosthesis within the body vessel when the inner lumen is pushed forward. This movement can lead to inaccurate positioning and, in some instances, possible perforation of the vessel wall by a protruding end of the prosthesis. Further, systems that utilize the actuating wire design will tend to move to follow the radius of curvature when placed in curved anatomy of the patient. As the wire is actuated, tension in the delivery system can cause the system to straighten. As the system straightens, the position of the prosthesis changes because the length of the catheter no longer conforms to the curvature of the anatomy. This change of the geometry of the system within the anatomy also leads to inaccurate prosthesis positioning.

Systems are known for delivering or implanting a self-expanding device in a vessel by operation of a balloon to rupture a sheath that holds the self-expanding device in a compressed state. When the device is located at the desired position in the vessel, the balloon is inflated, rupturing the sheath, thereby allowing the device to expand into position. Examples of these systems include U.S. Pat. Nos. 6,656,213 to Solem and 5,549,635 to Solar.

While Solem '213 and Solar '635 describe systems for delivering a self-expanding stent by operation of a balloon to rupture a sheath, experimental implementations of systems of these types of systems have shown results that fall short of expectations. In experiments on porcine coronary arteries, withdrawal of the catheter delivery system after sheath rupturing resulted in migration of the stent from the target implant position. The amount of stent migration was unpredictable and was in the range of 3-10 mm, which is suboptimal for the treatment of coronary lesions.

There are two primary structural factors that lead to stent migration for these systems. First the stent may remain circumferentially enclosed by the sheath at points along its length even after sheath rupture, i.e., the stent may not fully exit the sheath. Secondly, the friction between the sheath and the stent during catheter removal may drag the stent proximally. The inability of these systems to offer accurate placement of a stent at a target site causes this approach to be not optimum for treatment of coronary lesions and similar stenotic disease states.

There is thus a widely recognized need for, and it would be highly advantageous to have, a delivery system that is devoid of the above limitations.

SUMMARY

According to one aspect of the present disclosure there is provided a delivery system for a self-expanding prosthesis that includes a catheter having a distal portion and a proximal portion, a balloon disposed on the distal portion of the catheter, a self-expanding prosthesis disposed on at least a portion of the balloon, the self-expanding prosthesis having a compressed state and an expanded state, and a sheath coupling the self-expanding prosthesis to the balloon when the self-expanding prosthesis in its compressed state, the sheath including an opening in a wall of the sheath that initiates rupturing of the sheath so that the self-expanding prosthesis may move from its compressed state to its expanded state, and a distal end portion of the balloon that is distal to a distal end of the sheath including an enlarged diameter portion, the enlarged diameter portion having approximately the same outer diameter as an outer diameter of the sheath when the self-expanding prosthesis is in its compressed state, and the enlarged diameter portion being the maximum outer diameter of the balloon when the self-expanding prosthesis is in its compressed state.

According to another aspect of the present disclosure, there is provided a catheter having a distal portion and a proximal portion, a balloon disposed on the distal portion of the catheter, a self-expanding prosthesis disposed on at least a portion of the balloon, the self-expanding prosthesis having a compressed state and an expanded state, a sheath coupling the self-expanding prosthesis to the balloon when the self-expanding prosthesis is in its compressed state, the sheath including a slit in the wall of the sheath that initiates rupturing of the sheath so that the self-expanding prosthesis may move from its compressed state to its expanded state, a length of the slit extending not more than 5% a length of the sheath.

According to another aspect of the present disclosure, there is provided a method of deploying a self-expanding prosthesis, the method including expanding a balloon to initiate a rupture in a sheath along a distal opening in a wall of the sheath, the sheath coupling a self-expanding prosthesis to the balloon such that the self-expanding prosthesis is disposed between the balloon and the sheath when the self-expanding prosthesis is in a compressed state, controllably continuing the rupture of the sheath from the distal opening to a proximal end of the sheath thereby allowing the self-expanding prosthesis to move from its compressed state to an expanded state, a distal end portion of the sheath that is distal to a distal end of the sheath including an enlarged diameter portion, the enlarged diameter portion having approximately the same outer diameter as an outer diameter of the sheath when the self-expanding prosthesis is in its compressed state, and the enlarged diameter portion being the maximum outer diameter of the balloon when the self-expanding prosthesis is in its compressed state.

Unless otherwise defined, all technical and scientific terms used herein have the same meaning as commonly understood by one of ordinary skill in the art. In addition, the materials, methods, and examples are illustrative only and are not intended to be limiting.

BRIEF DESCRIPTION OF THE DRAWINGS

With specific reference now to the drawings in detail, it is stressed that the particulars shown are by way of example and for purposes of illustrative discussion of the various embodiments of the present disclosure only, and are presented in the cause of providing what is believed to be the most useful and readily understood description of the principles and conceptual aspects. In this regard, no attempt is made to show structural details of the disclosed embodiments in more detail than is necessary for a fundamental understanding, the description taken with the drawings making apparent to those skilled in the art how the several forms of the disclosed embodiments may be embodied in practice.

In the drawings:

FIG. 1A is a longitudinal cross-sectional illustration of a delivery system in accordance with embodiments;

FIG. 1B is a transverse cross-sectional illustration of a delivery system in accordance with the embodiments shown in FIG. 1A;

FIG. 3A is a longitudinal cross-sectional illustration of a delivery system in accordance with another embodiment;

FIG. 3B is a transverse cross-sectional illustration of a delivery system in accordance with the embodiment shown in FIG. 3A;

DETAILED DESCRIPTION

Figure 2A:
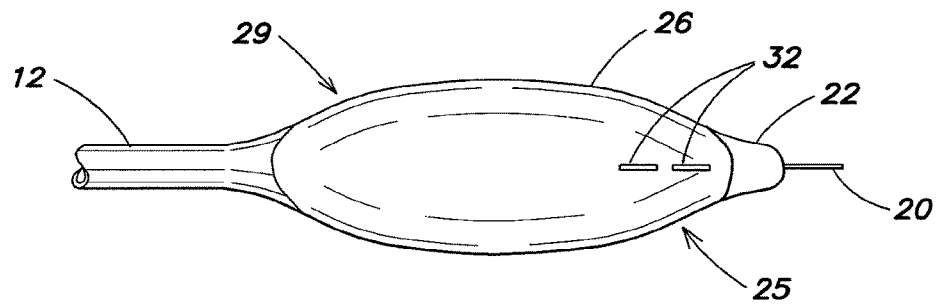
FIGS. 2A-2E are perspective illustrations of a distal end of a catheter having a sheath and showing openings on the sheath.

The present disclosure is directed to a delivery system for deployment of a prosthesis in a vessel. Specifically, the embodiments of the present disclosure can be used to deploy a self-expandable prosthesis at an ostium or bifurcation using a balloon controllable sheath.

The principles and operation of a delivery device and methods according to the present disclosure may be better understood with reference to the drawings and accompanying descriptions.

Before explaining at least one embodiment of the present disclosure in detail, it is to be understood that the disclosure is not limited in its application to the details of construction and the arrangement of the components set forth in the following description or illustrated in the drawings. The embodiments disclosed herein are capable of being practiced or carried out in various ways. Also, it is to be understood that the phraseology and terminology employed herein are for the purpose of description and should not be regarded as limiting.

It is appreciated that certain features of the disclosure, which are, for clarity, described in the context of separate embodiments, may also be provided in combination in a single embodiment. Conversely, various features of the disclosure which are, for brevity, described in the context of a single embodiment, may also be provided separately or in any suitable subcombination.

Reference is now made to FIG. 1A and FIG. 1B, which are longitudinal and transverse cross-sectional illustrations, respectively, of a delivery system 10 in accordance with embodiments of the present disclosure. Delivery system 10 includes a catheter 12 having a proximal end 14 and a distal end 16. The catheter 12 has at least one guidewire lumen 18 for receiving a guidewire 20 therethrough. In alternative embodiments, two or more guidewire lumens 18 are provided, either coaxial with, or adjacent to, one another. A balloon 22 is positioned on distal end 16 of catheter 12 and is in fluid communication with an inflation lumen 23. Inflation lumen 23 runs proximally along the length of catheter 12 from balloon 22 to an inflation port 30 located at a hub 28. Fluid, which may be a liquid or gas, is introduced into inflation port 30, and runs through inflation lumen 23 and into balloon 22, thereby expanding balloon 22. Such techniques are commonly known in the art. In one embodiment, inflation lumen 23 is positioned coaxially with respect to catheter 12, but may also be adjacent thereto. Guidewire lumen 18 has an exit port 21 at a proximal end thereof. In one embodiment, exit port 21 is positioned relatively close to a proximal end of balloon 22 for rapid exchange capabilities. In an alternative embodiment, exit port 21 is located at proximal end 14 of catheter 12.

A self-expandable prosthesis 24 is positioned around balloon 22 in a collapsed state and is held in place, or coupled thereto, by a sheath 26 at least partially surrounding prosthesis 24. In one embodiment, self-expandable prosthesis 24 is comprised of a shape memory metal or super-elastic Nickel Titanium alloy such as Nitinol™. In alternative embodiments, prosthesis 24 has elastic properties due to design characteristics such as the use of spring-like connectors. In some embodiments, prosthesis 24 may include any material known to one of skill in the art such as, for example, stainless steel, Elgiloy, nickel, titanium, platinum, gold, polymeric materials including PMA, PTFE, ePTFE, and other materials. Prosthesis 24 may be self-expandable or balloon-expandable. In general, prosthesis 24 is designed to self-expand in the absence of a retaining element such as sheath 26. As shown in FIG. 1A and FIG. 1B, prosthesis 24 is sandwiched between balloon 22 and sheath 26. Sheath 26 includes a prosthesis-enclosing portion 36 and a catheter-enclosing portion 38. While the catheter-enclosing portion 38 is shown proximal to the balloon 22, the catheter-enclosing portion 38 can also be located distal to the balloon 22.

Expansion of balloon 22 results in a controlled separation, and thus opening, of prosthesis-enclosing portion 36 of sheath 26. Once prosthesis-enclosing portion 36 of sheath 26 opens, prosthesis 24 is released and is free to self-expand. In one embodiment, catheter-enclosing portion 38 of sheath 26 remains at least partially attached to catheter 12 after opening, at either of a location proximal or distal to the balloon 22, and sheath 26 is removed along with catheter 12 from the body. In another embodiment, prosthesis-enclosing portion 36 of sheath 26 completely detaches from catheter 12 and remains in the vessel with prosthesis 26, as will be described in further detail hereinbelow.

Reference is now made to FIGS. 2A-2E, which are perspective illustrations of distal end 16 of catheter 12 showing sheath 26 in accordance with various embodiments of the present disclosure. Sheath 26 includes at least one opening or cut or tear 32, in a wall of sheath 26, for providing an initial direction of separation of the sheath 26 upon balloon expansion. In some embodiments, opening 32 may include one or more slits in a wall of sheath 26. When balloon 22 is expanded, separation or opening of sheath 26 begins at a location defined by at least one opening 32. In some embodiments, more than one opening 32 is used. In one embodiment, at least one opening 32 is positioned at a distal end 25 of sheath 26, as shown in FIG. 2A. The at least one opening 32, in one embodiment, is a cut or slit extending longitudinally from the distal end 25 of the sheath. In one embodiment, the cut or slit extends not more than approximately 5% of the length of the sheath 26. In some embodiments, separating of sheath 26 originates at distal end 25, and a proximal end 29 of prosthesis-enclosing portion 36 of sheath 26 remains attached to catheter 12. In an alternate embodiment, separation of sheath 26 originates at the proximal end 29 and the distal end 25 of prosthesis enclosing portion 36 of sheath 26 remains attached to catheter 12. After deployment of prosthesis 24, sheath 26 may be removed along with catheter 12. The disclosed embodiments include various locations for openings 32 on sheath 26 such that the separation or opening of sheath 26 may extend proximally to distally along the length of sheath 26, distally to proximally along the length of sheath 26, middle to proximally along the length of sheath 26, or middle to distally along the length of sheath 26.

In accordance with embodiments, sheath 26 is comprised of, or coated with on either, or both of, an inner and outer surface, a low friction material, such as, but not limited to, for example, Teflon™, polytetrafluoroethylene (PTFE), fluorinated ethylene propylene (FEP), PFA, ETFE, or any synthetic hydrogel polymer including formulations based on HEMA, PVP, PEG and similar compounds, or other low friction biocompatible materials. The provision of such low-friction materials is to facilitate that sheath 26 can be pulled out from between prosthesis 26 and the vessel wall without becoming permanently trapped, without damaging either prosthesis 24 or the vessel wall, and without displacing or moving the prosthesis 24 from its intended location.

Figure 2B:
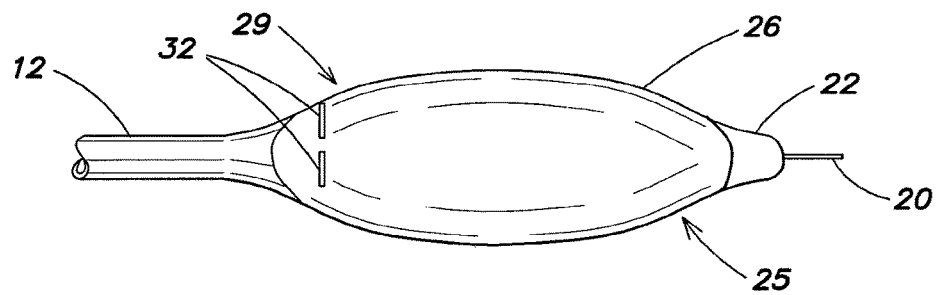

In another embodiment, at least one opening 32 is positioned at proximal end 29 of prosthesis-enclosing portion 36 of sheath 26, as shown in FIG. 2B. In this embodiment, separation of sheath 26 originates at proximal end 29 of prosthesis-enclosing portion 36. Most of sheath 26 detaches from catheter 12, and remains after deployment of prosthesis 24. In one embodiment, prosthesis-enclosing portion 36 of sheath 26 is comprised of a biodegradable material, such as a biodegradable polymer, so that it can safely disintegrate over time within the body.

Figure 2C:
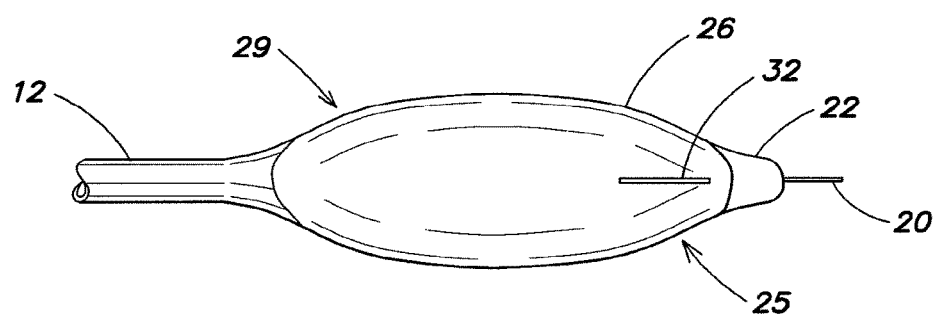
Figure 2D:
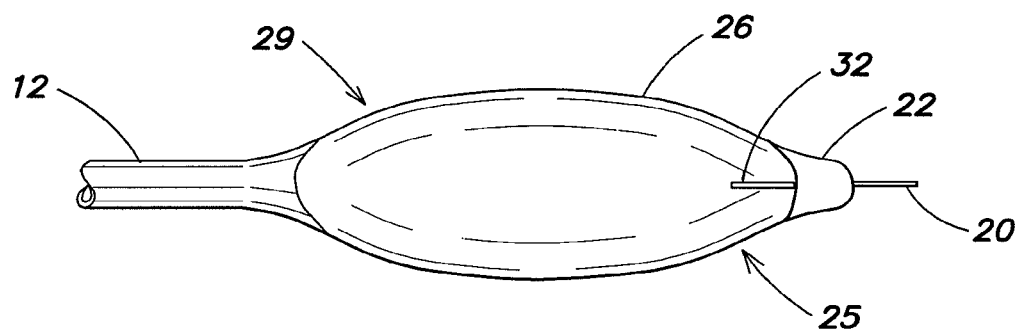
Figure 2E:
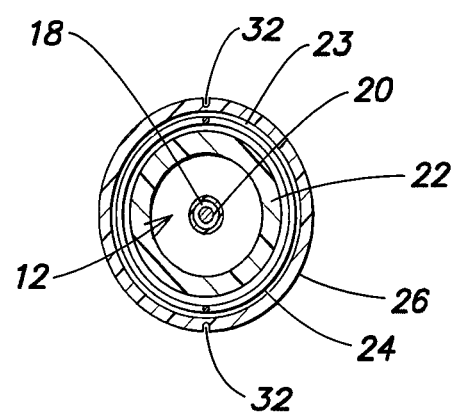

In alternative embodiments, several openings 32 and locations for openings 32 are used. For example, a combination of the distal and proximal openings 32 described above with respect to FIGS. 2A and 2B may be used, allowing for origination of separation at distal end 25 and detachment of sheath 26 from catheter 12. Any other combination of openings is possible, and openings may further have various geometric configurations, allowing for a high degree of control over the opening of sheath 26. For example, opening 32 may be located a distal end portion of sheath 26, as shown in FIG. 2C. Additionally, opening 32 may be located at a distalmost end of sheath 26, as shown in FIG. 2D. Opening 32 may include a single slit on sheath 26 or a plurality of slits. As shown, for example, in FIG. 2A, the slits may be linearly arranged. Additionally or alternatively, the slits may be radially arranged and/or may extend circumferentially around sheath 26 such that the slits are parallel along a longitudinal axis of sheath 26. For example, as shown in FIG. 2E, the slits (openings 32) may be arranged circumferentially around a distal cross-section of sheath 26. In some embodiments, one or more slits may extend along a grain longitudinal direction of sheath 26.

The several openings 32 may be located in the surface of the sheath 26 such that upon inflation of the balloon 22, as discussed, the sheath 26 separates but remains attached to the catheter 12, In one embodiment, the several openings 32 may be located proximally, similar to that shown in Fig, 2B, where the sheath 26 remains attached to the catheter 12 at a distal end thereof. Further, in one embodiment of the present disclosure, the several openings 32 are provided such that the sheath 26, upon separation, results in multiple sections remaining attached to the catheter 12 similar to petals on a flower.

In some embodiments, as shown in FIG. 2C, at least one opening 32 is offset a predetermined distance from the distal end 25 of the sheath. Thus, opening 32 may facilitate the separation or tearing of the sheath 26 longitudinally toward each of the distal end 25 and the proximal end 29 upon expansion of the balloon 22.

Reference is now made to FIG. 3A and FIG. 3B, which are, respectively, longitudinal and transverse cross-sectional illustrations of delivery system 100 in accordance with another embodiment. Delivery system 100 includes catheter 12 with proximal end 14 and distal end 16. Catheter 12 has at least one guidewire lumen 18 for receiving guidewire 20 therethrough. In alternative embodiments, two or more guidewire lumens 18 are provided, either coaxial with, or adjacent to, one another. Balloon 22 is positioned on distal end 16 of catheter 12, and is in fluid communication with inflation lumen 23. Inflation lumen 23 runs proximally along the length of catheter 12 from balloon 22 to inflation port 30 located at hub 28. Fluid introduced through inflation port 30 runs through inflation lumen 23 and into balloon 22, thereby expanding balloon 22. Fluid may be liquid or air, and such configurations are commonly known in the art. In one embodiment, inflation lumen 23 is positioned coaxially with respect to catheter 12, but may also be adjacent thereto. Guidewire lumen 18 has an exit port 21 at a proximal end thereof. Exit port 21 is located at proximal end 14 of catheter 12.

Self-expandable prosthesis 24 is positioned around balloon 22 in a collapsed state and is held in place, or coupled thereto, by sheath 26 having a prosthesis-enclosing portion 36 and a catheter-enclosing portion 38. In one embodiment, self-expandable prosthesis 24 is comprised of a shape memory metal or super-elastic Nickel Titanium alloy such as Nitinol™. In alternative embodiments, prosthesis 24 has elastic properties due to design characteristics such as the use of spring-like connectors. In general, prosthesis 24 is designed to self-expand in the absence of a retaining element such as sheath 26. As shown in FIG. 3A and FIG. 3B, prosthesis 24 is sandwiched between balloon 22 and sheath 26.

Expansion of balloon 22 results in a controlled separation of prosthesis-enclosing portion 36 of sheath 26, thereby releasing prosthesis 24 and allowing it to expand.

In delivery system 100 shown herein, catheter-enclosing portion 38 of sheath 26 extends proximally along the outside of catheter 12, and has a handle 34 at a proximal end thereof. After deployment of prosthesis 24, sheath 26 is pulled back via handle 34 prior to deflation of balloon 22 and removal of catheter 12. In accordance with this embodiment, sheath 26 is comprised of a low friction material, such as, for example, Teflon™, or other low friction biocompatible materials, to ensure that sheath 26 can be removed from between prosthesis 24 and the vessel wall. More specifically, a material of sheath 26 is chosen such that the friction between sheath 26 and prosthesis 24 is significantly lower than the friction between prosthesis 24 and balloon 22. Alternatively, friction-increasing elements may be added to an outer surface of balloon 22, in order to increase the frictional coefficient between prosthesis 24 and balloon 22.

Figure 4:
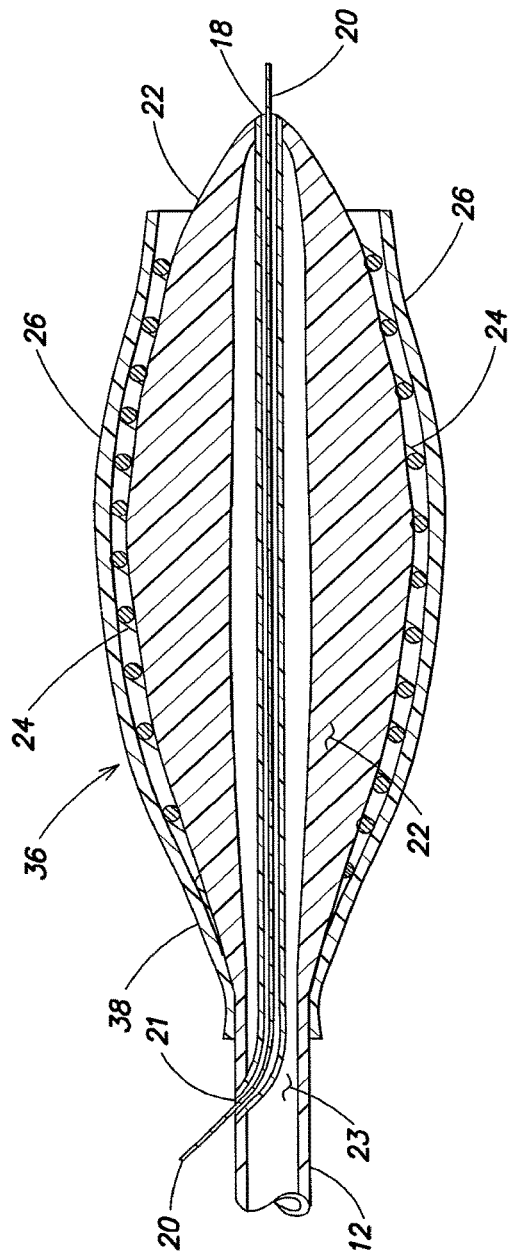
FIG. 4 is a cross-sectional illustration of embodiments of the delivery system during expansion of a balloon.

Reference is now made to FIG. 4, which is a cross-sectional illustration of delivery system 10 during expansion of balloon 22, in accordance with one embodiment. As balloon 22 expands via fluid introduced through inflation lumen 23, sheath 26 begins to separate, and prosthesis 24 begins to expand. As sheath 26 separates, prosthesis 24 deploys into its fully open state. As shown in FIG. 4, the sheath 26 is separating from its distal end.

Figure 5:
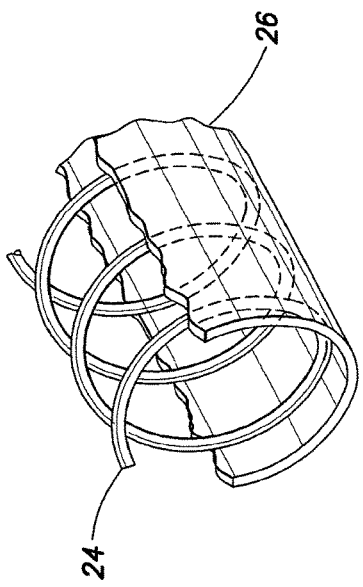
FIG. 5 is a perspective view illustration of a prosthesis in its fully expanded state, and a sheath fully open, in accordance with embodiments.

Reference is now made to FIG. 5, which is a perspective view illustration of prosthesis 24 in its fully expanded state, and sheath 26 fully separated. It should be readily apparent that because sheath 26 is not made of an expandable material, it is smaller than the expanded circumference of prosthesis 24 after deployment. Thus, only a portion of prosthesis 24 is surrounded by sheath 26 after deployment, as shown in FIG. 5. At least a portion of sheath 26 remains located between prosthesis 24 and the vessel wall after deployment. In a first embodiment, the remaining portion of sheath 26 is pulled out along with catheter 12. In a second embodiment, the remaining portion of sheath 26 remains in the vessel. In a third embodiment, the remaining portion of sheath 26 is pulled out prior to removal of catheter 12.

Figure 10:
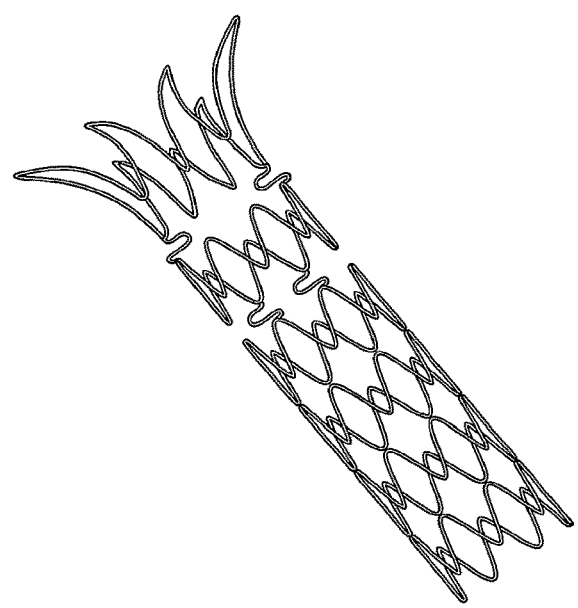
FIG. 10 is an ostial protection device.

Prosthesis 24 is depicted as a cylinder for illustrative purposes only and should not be limited to this shape or configuration. Prosthesis 24 can be any self-expandable device which can be placed within a vessel. In one embodiment, prosthesis 24 is an ostial device as shown in FIG. 10 or such as one described more fully in U.S. patent application Ser. No. 11/095,983, filed on Mar. 31, 2005 and published as U.S. Publication 2005/0222672 on Oct. 6, 2005 and which is incorporated by reference herein in its entirety. In alternative embodiments, prosthesis 24 is any bifurcation stent, drug coated stent, graft or any other self-expandable vascular device.

Figure 6A:
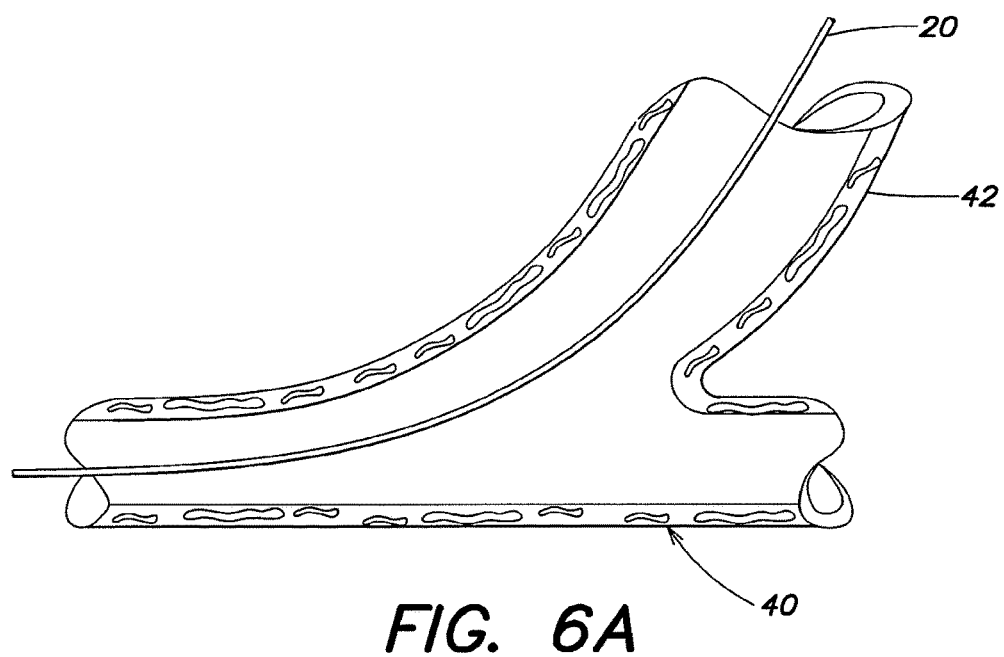
FIGS. 6A-6E are illustrations of steps of a method of deployment of a prosthesis within a vessel in accordance with embodiments.

Reference is now made to FIGS. 6A-E, which are illustrations of steps of a method of deployment of prosthesis 24 within a vessel in accordance with one embodiment of the present disclosure. First, guidewire 20 is inserted into a main vessel 40. In one embodiment, guidewire 20 is further advanced into a branch vessel 42, as shown in FIG. 6A. This embodiment is useful when deploying an ostial device into an ostium or side branch. In an alternative embodiment, guidewire 20 is advanced through main vessel 40 for deployment of a prosthesis at a main vessel lesion. In alternative embodiments, more than one guidewire may be used, for example, for bifurcation stent delivery.

Figure 6B:
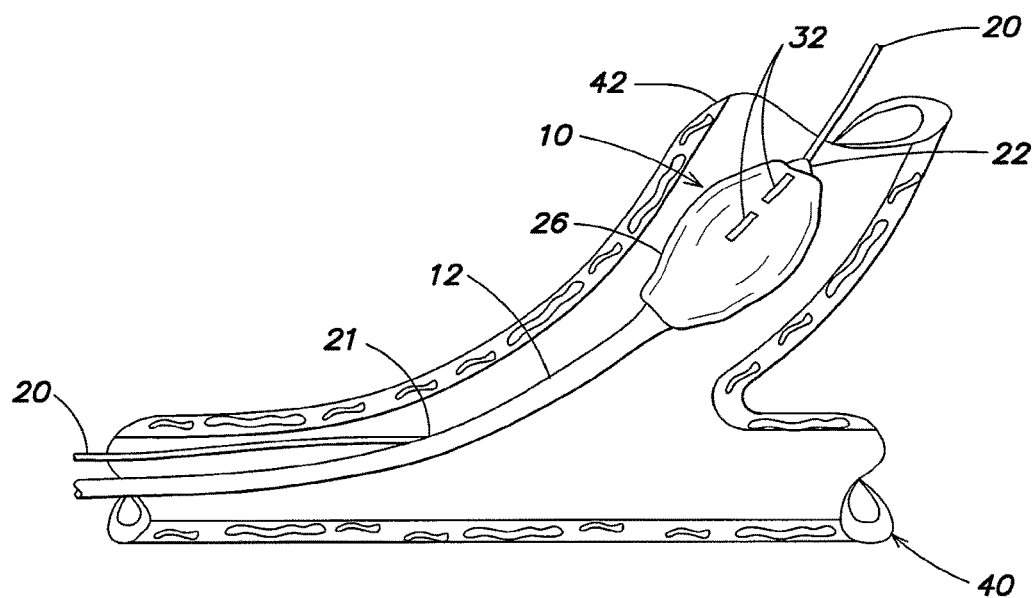
Figure 6C:
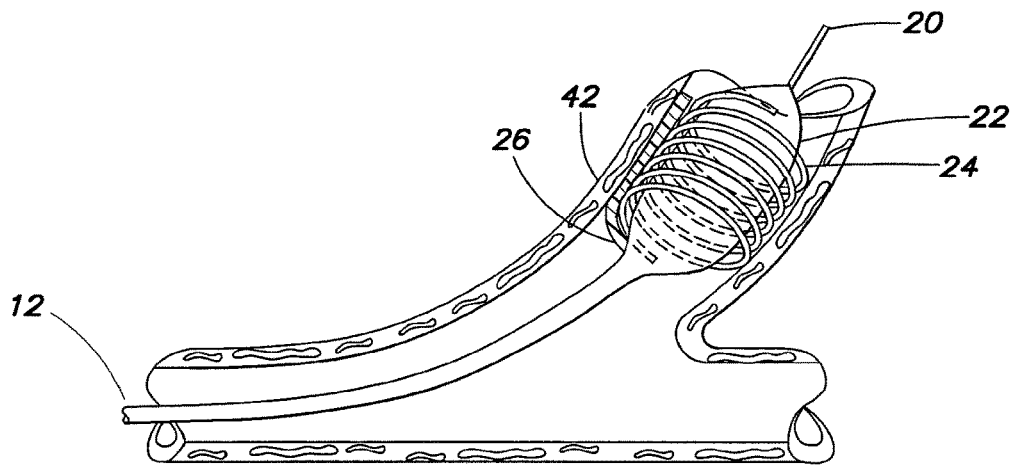
Figure 6D:
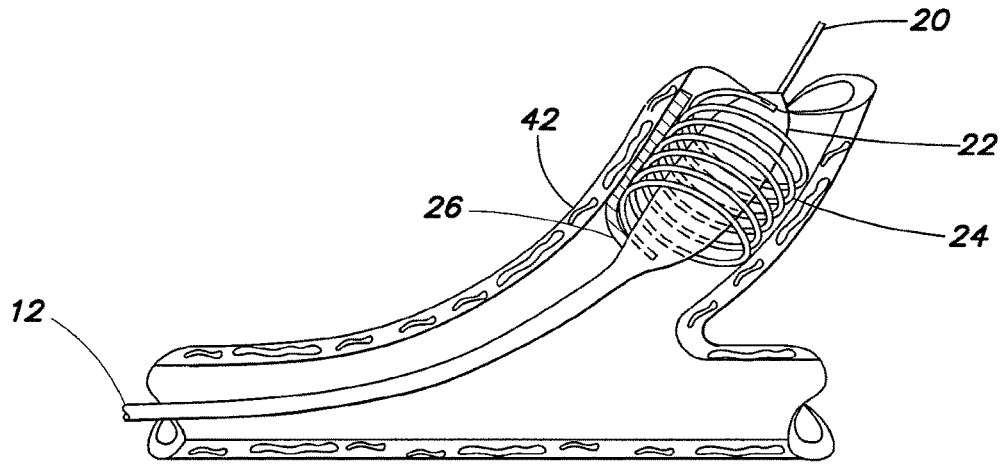
Figure 6E:
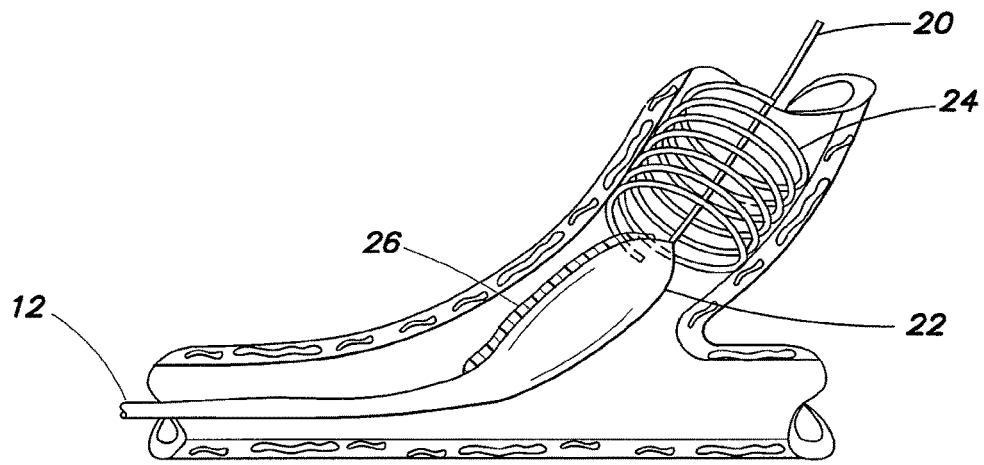

Delivery system 10 is advanced over guidewire 20 until in position, as shown in FIG. 6B. Balloon 22 is then expanded, causing separation of sheath 26 originating at opening(s) 32 at a distal end of delivery system 10. This expansion of the balloon 22 causes release of prosthesis 24 from catheter 12. Prosthesis 24 is deployed, placing at least a portion of sheath 26 between prosthesis 24 and a wall of branch vessel 42, as shown in FIG. 6C. Balloon 22 is then deflated, as shown in FIG. 6D. Finally, catheter 12 with sheath 26 attached thereto is removed from the branch vessel 42 and then from the patient via main branch 40, as shown in FIG. 6E.

Reference is now made to FIGS. 7A-D, which are illustrations of steps of a method of deployment of prosthesis 24 within a vessel in accordance with another embodiment of the present disclosure. First, guidewire 20 is inserted into a main vessel 40. In one embodiment, guidewire 20 is further advanced into a branch vessel 42, as shown in FIG. 6A. This embodiment is also useful when deploying an ostial device. In an alternative embodiment, guidewire 20 is advanced through main vessel 40 for deployment of a stent at a main vessel lesion. In alternative embodiments, more than one guidewire may be used, for example, for bifurcation stent delivery.

Figure 7A:
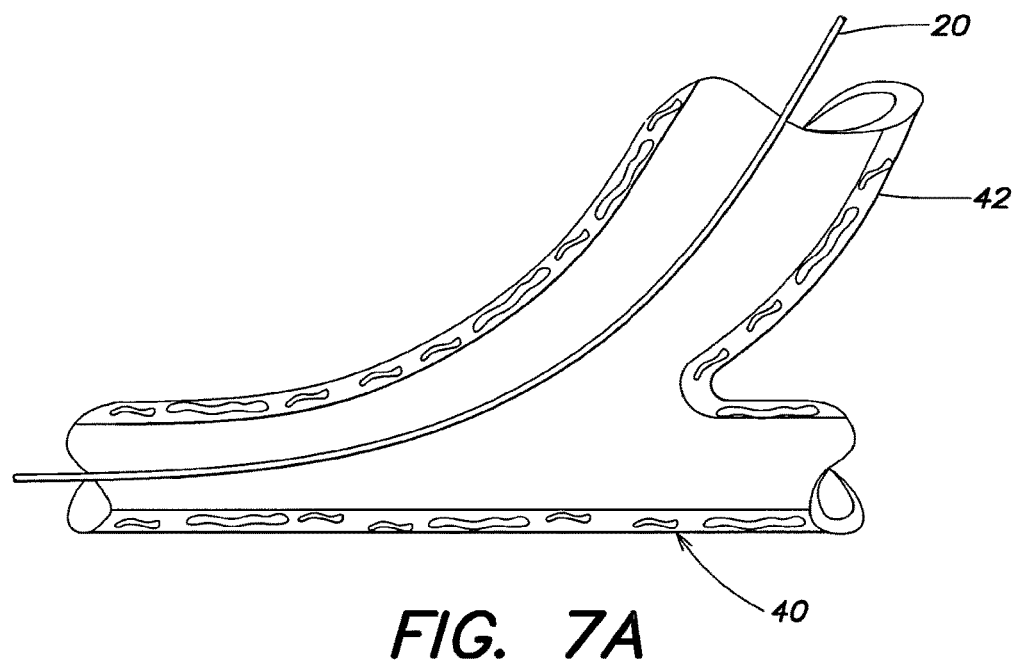
FIGS. 7A-7D are illustrations of steps of a method of deployment of a prosthesis within a vessel in accordance with embodiments.
Figure 7B:
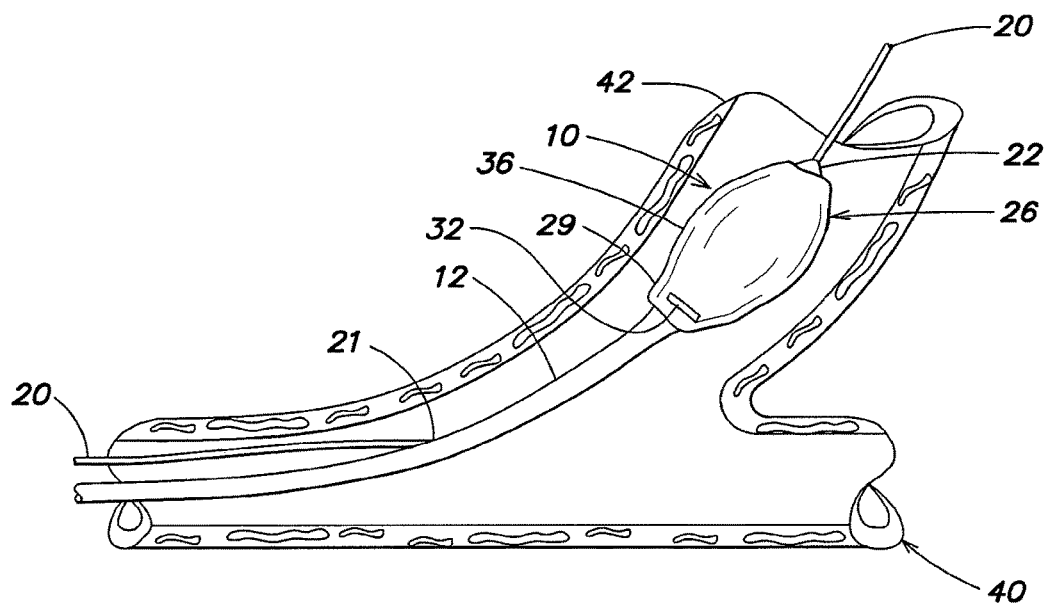
Figure 7C:
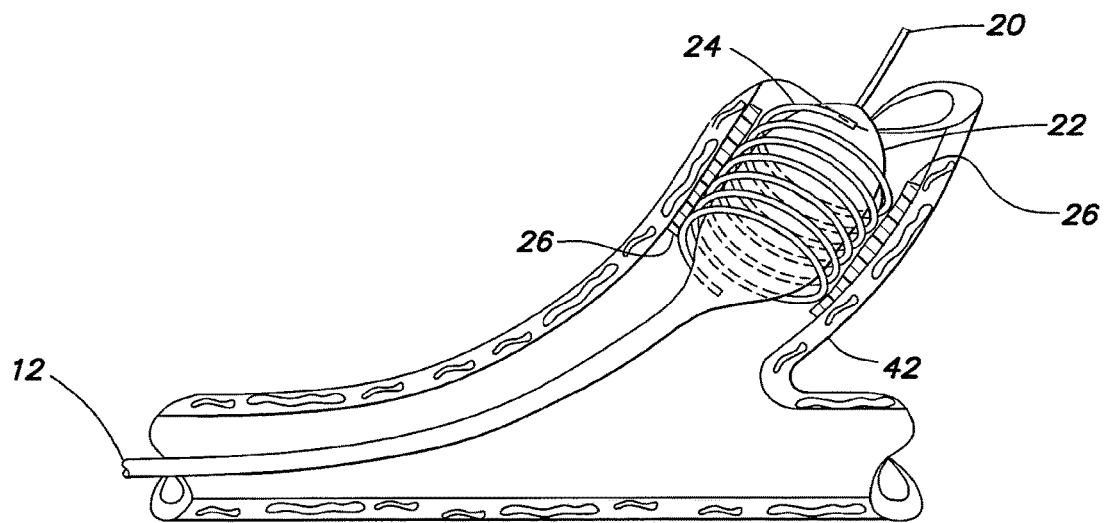
Figure 7D:
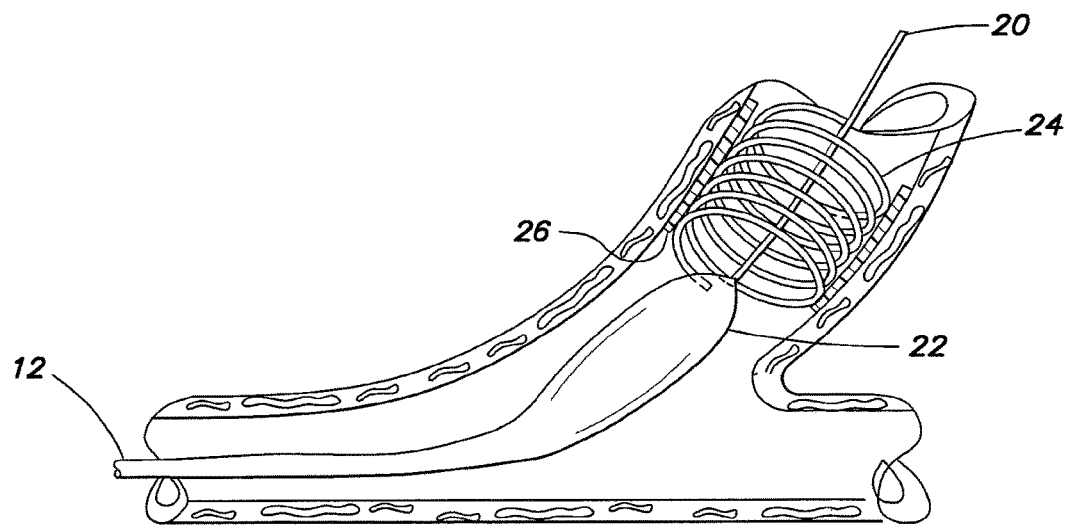

Delivery system 10 is advanced over guidewire 20 until in position, as shown in FIG. 7B. Balloon 22 is then expanded, causing separation of sheath 26 originating at opening(s) 32, shown at proximal end 29 of prosthesis-enclosing portion 36 of sheath 26. The expansion of balloon 22 causes release of sheath 26 from catheter 12. Prosthesis 24 is deployed, placing at least a portion of sheath 26 between prosthesis 24 and a wall of side vessel 42, as shown in FIG. 7C. Balloon 22 is then deflated, and catheter 12 is removed from the vessel, as shown in FIG. 7D. Sheath 26 remains in the vessel, and may be comprised of either a biodegradable material, a physiologically inert material or a combination thereof.

Figure 8A:
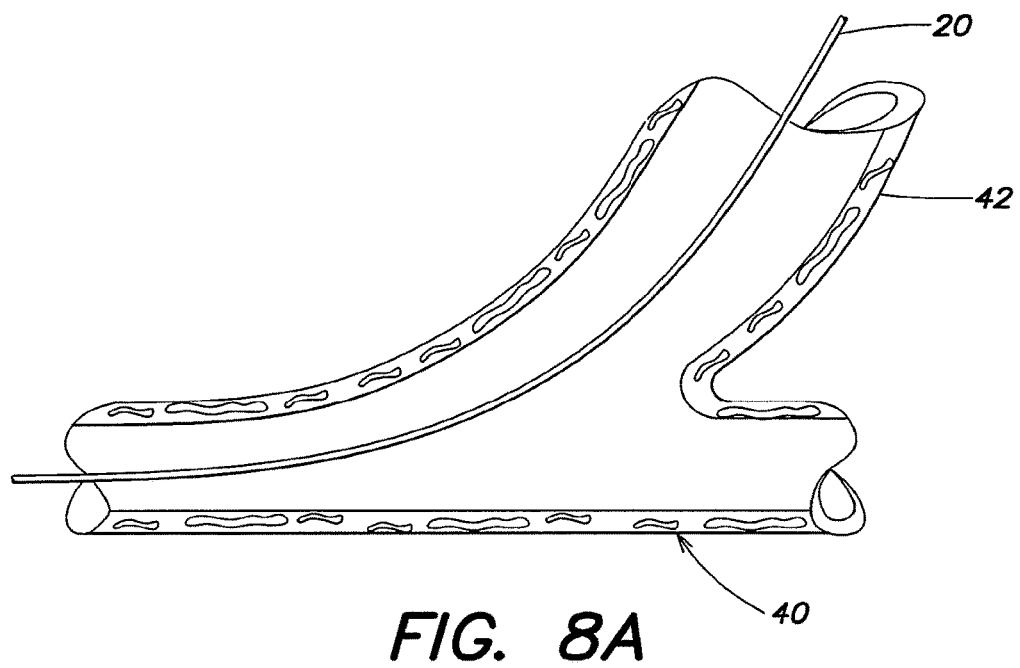
FIGS. 8A-8E are illustrations of steps of a method of deployment of a prosthesis within a vessel in accordance with embodiments.
Figure 8B:
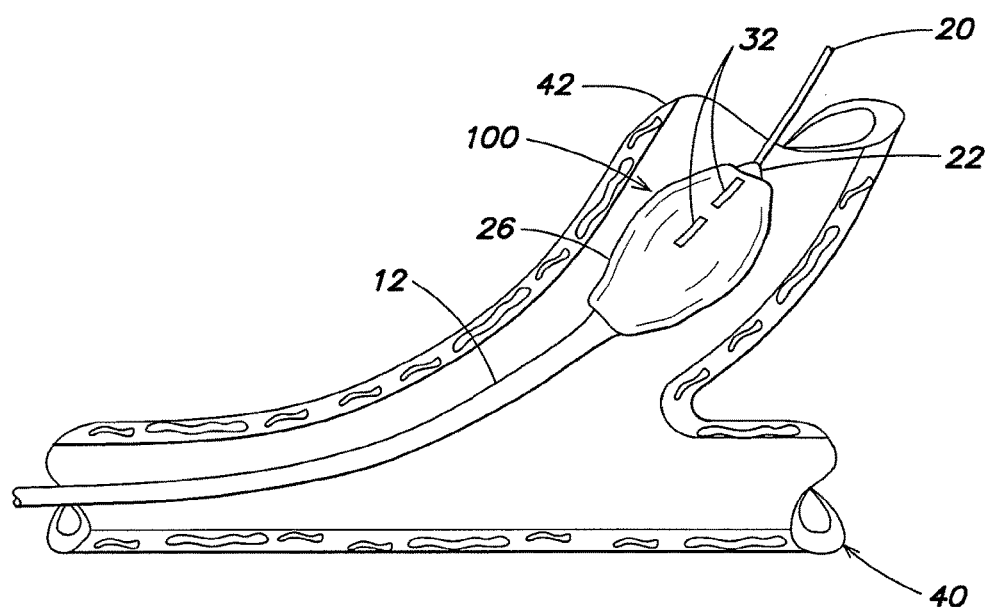
Figure 8C:
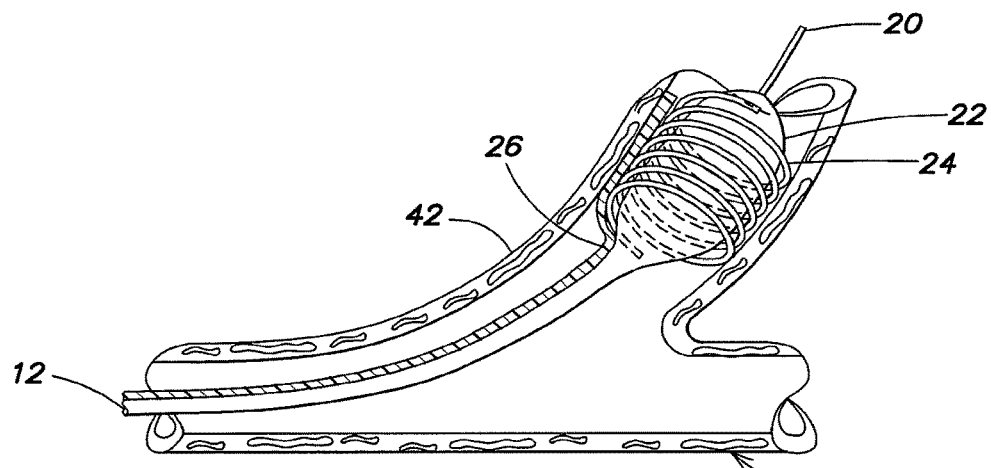
Figure 8D:
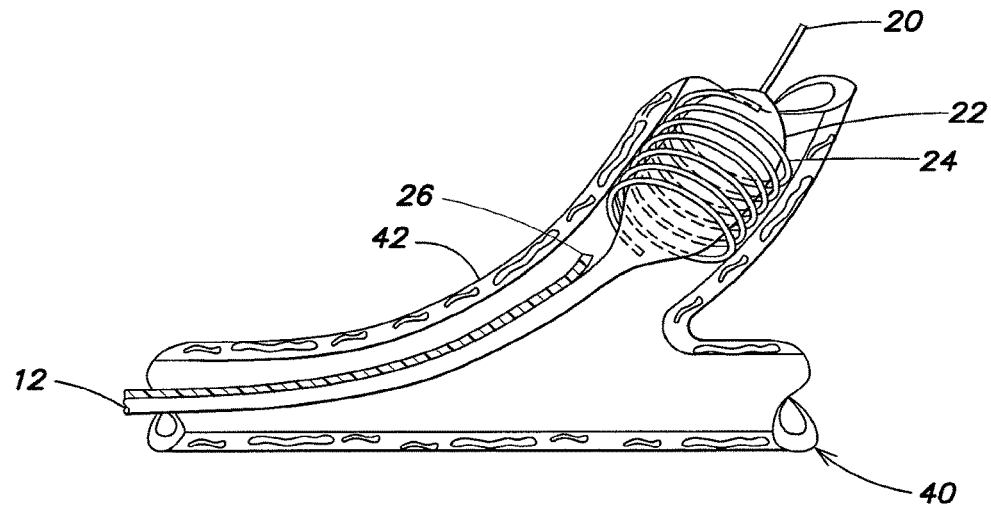
Figure 8E:
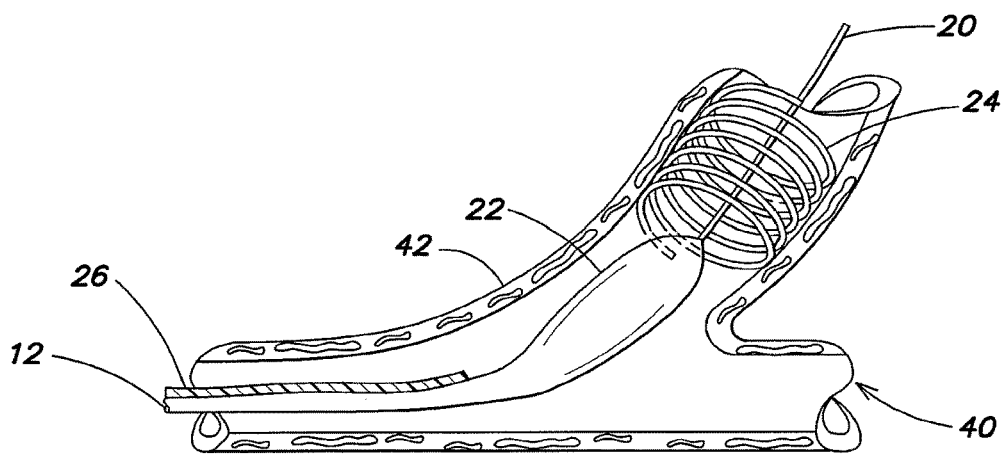

Reference is now made to FIGS. 8A-E, which are illustrations of steps of a method of deployment of prosthesis 24 within a vessel in accordance with another embodiment method using the system 100. First, guidewire 20 is inserted into side vessel 42 via a main vessel 40 similar to that which has been described with reference to FIGS. 6 and 7. Delivery system 100 is advanced over guidewire 20 until in position, as shown in FIG. 8B. Balloon 22 is then expanded, causing separation of sheath 26 originating at opening(s) 32 at a distal end of system 100. This expansion of the balloon 22 causes release of prosthesis 24 from catheter 12. Prosthesis 24 is deployed, locating sheath 26 between prosthesis 24 and a wall of side vessel 42, as shown in FIG. 8C. Sheath 26 is then pulled back from between the prosthesis 24 and the wall of the side vessel 42, as shown in FIG. 8D. Finally, balloon 22 is deflated, and catheter 12 and sheath 26 are removed from the main vessel 40, as shown in FIG. 8E.

Figure 9A:
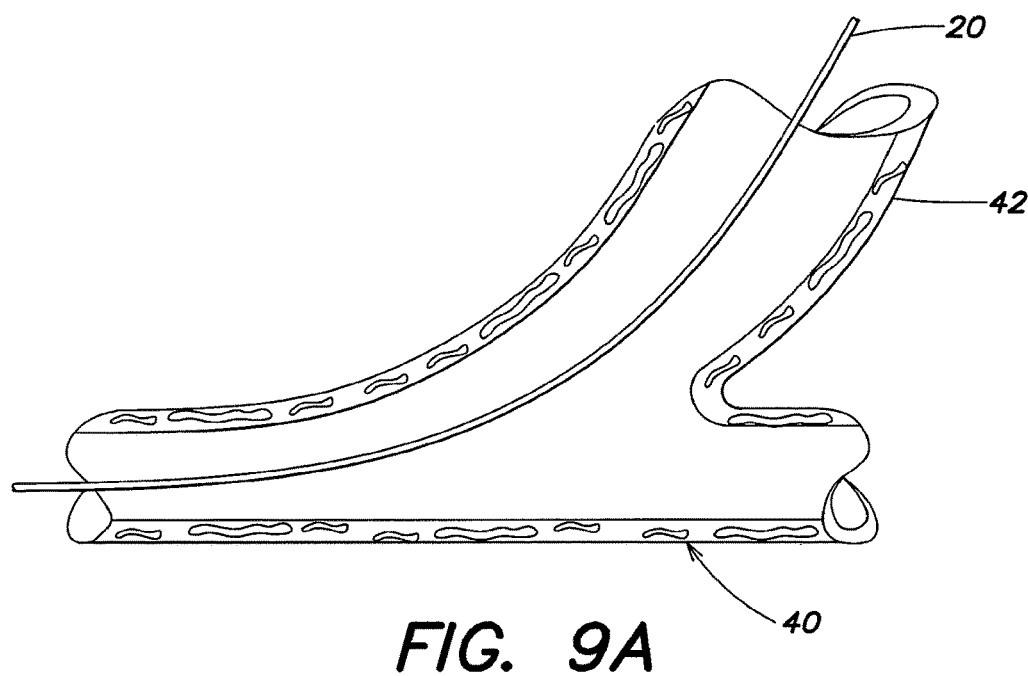
FIGS. 9A-9G are illustrations of steps of a method of deployment of a prosthesis within a vessel in accordance with embodiments.
Figure 9B:
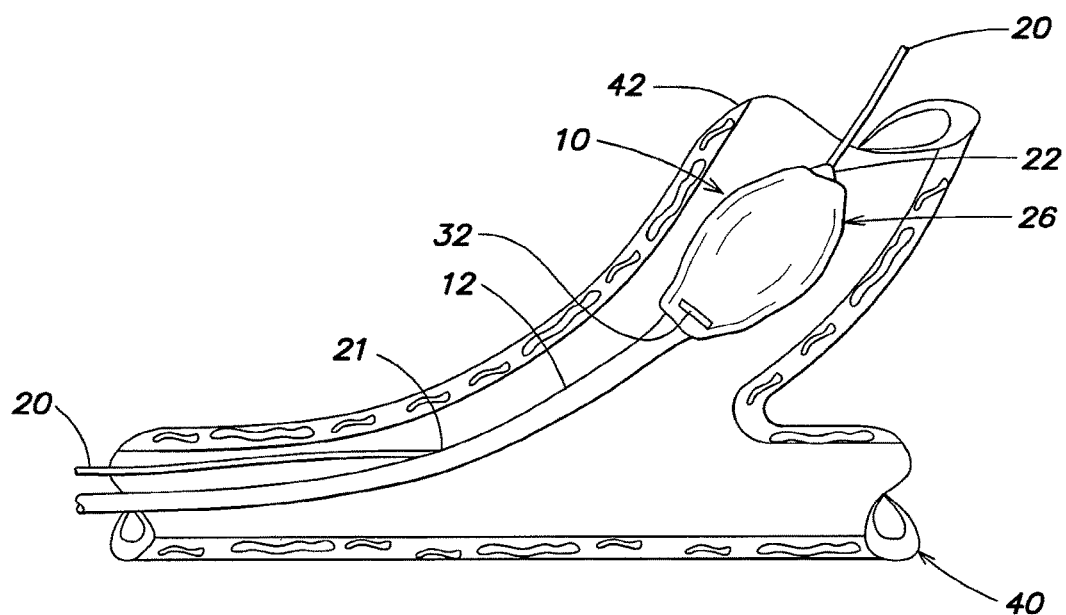
Figure 9C:
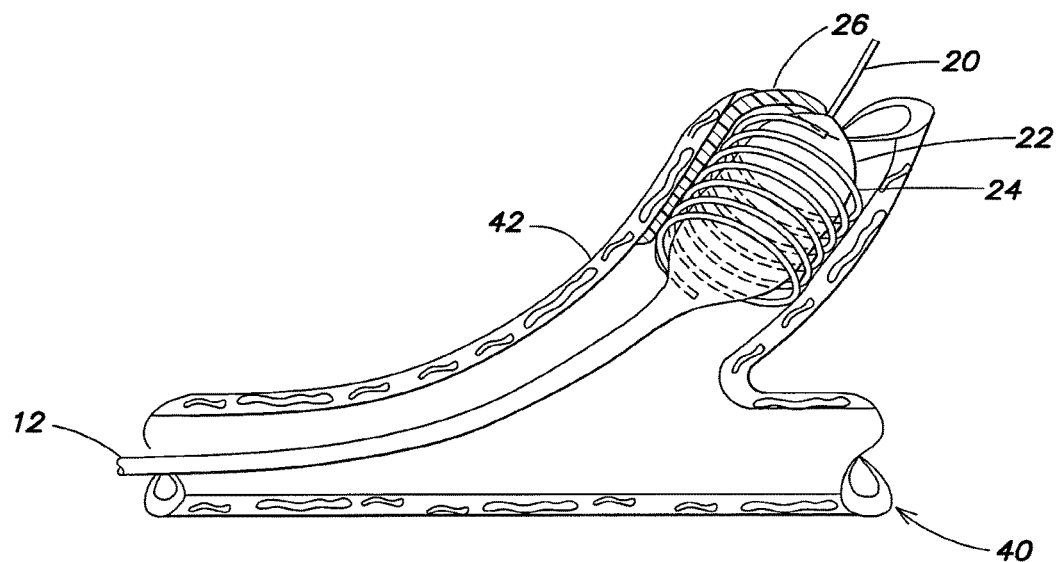
Figure 9D:
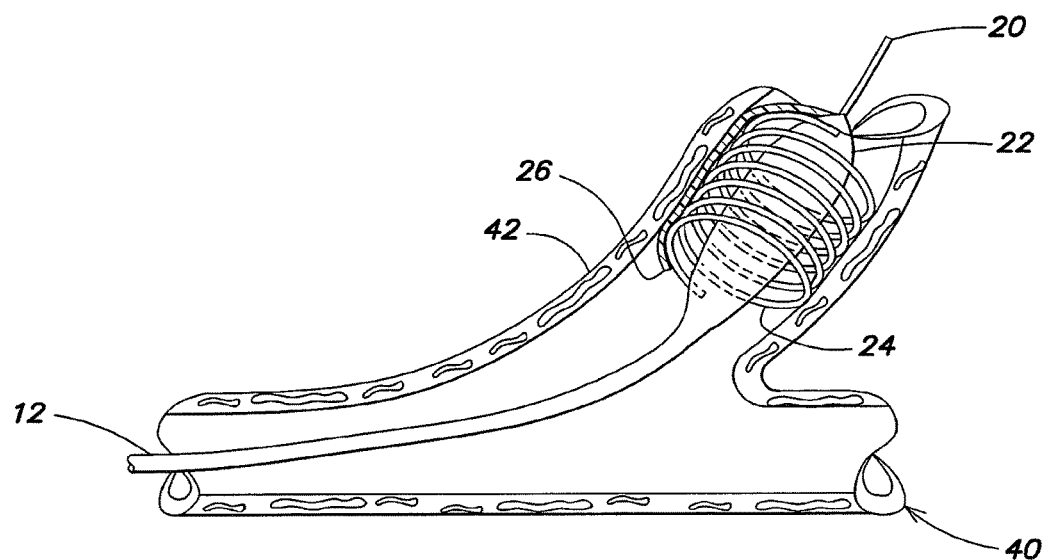

In an alternate method as shown in FIGS. 9A-9G, a method for placing a prosthesis 24 is provided. Here, the delivery system 10 is provided with sheath 26 and opening(s) 32 such that the sheath 26 remains attached to the catheter 12 at a point distal to the balloon 22. As shown in FIGS. 9A and 9B, similar to that described above with respect to FIGS. 6A and 6B, 7A and 7B and 8A and 8B, the catheter 12 is positioned within a side vessel 42 as guided by a guide wire 20. Upon expansion of the balloon 22, the sheath 26 separates but remains attached to the catheter 12 as shown in FIG. 9C. The separation of the sheath 26 allows the self-expanding device 24 to expand as shown in FIG. 9D.

Figure 9E:
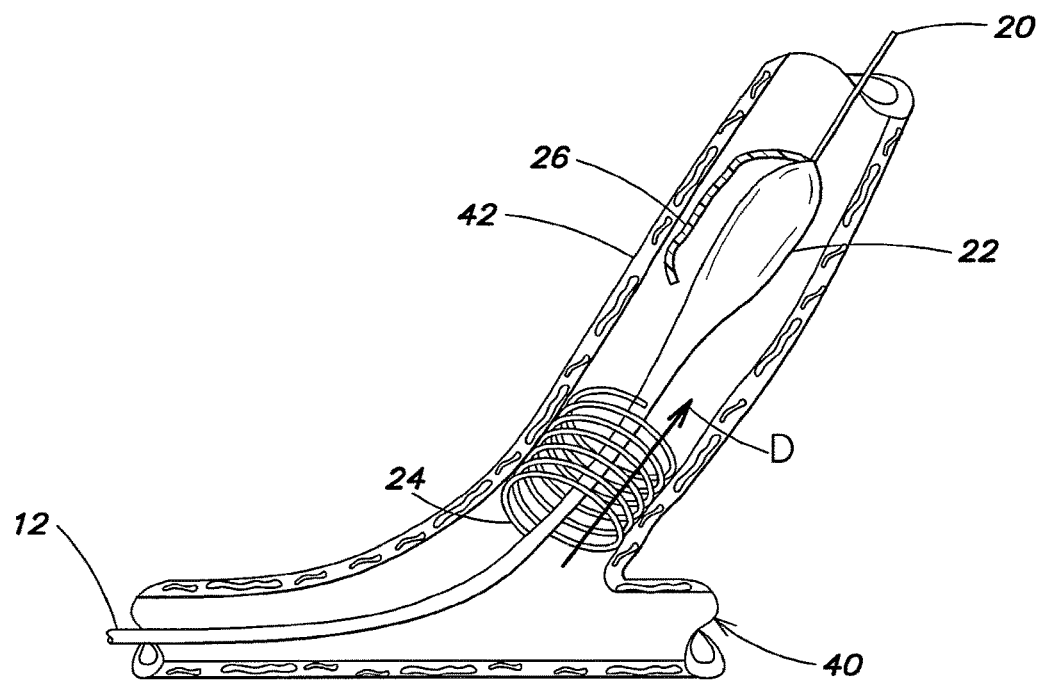

Subsequently, as shown in FIG. 9E, the balloon 22 is deflated and the catheter 12 is then advanced further, in the direction shown by the arrow D, into the side vessel 42. The separated sheath 26 is removed from between the expanded prosthesis 24 and a wall of the side vessel 42 upon the movement of the catheter further into the side vessel 42. Where the prosthesis 24 is an ostial device, advantageously, the insertion of the catheter 12 further into the side vessel 42 and the subsequent removal of the sheath 26 from between the prosthesis 24 and the wall of the side vessel 42 may operate to better position the device 24 at the ostium.

Figure 9F:
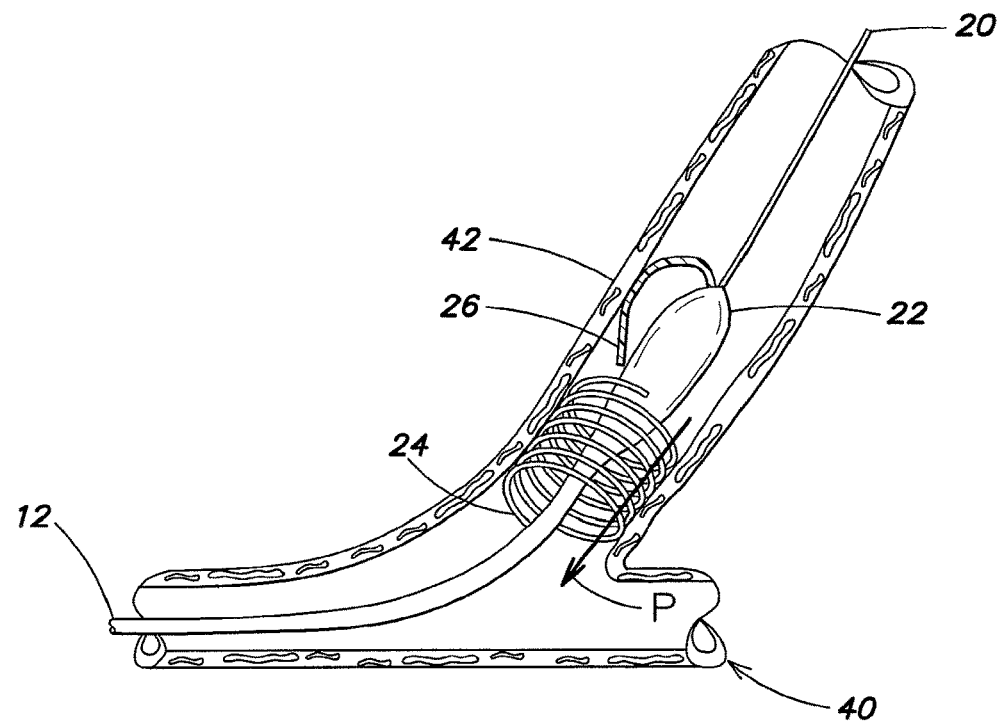
Figure 9G:
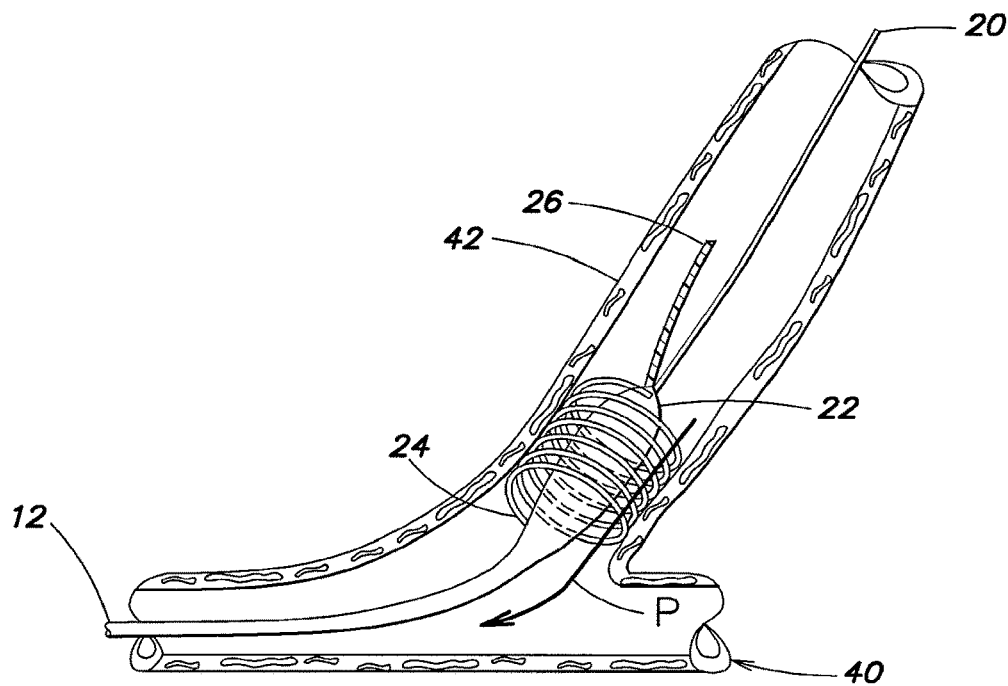

Once the catheter 12 has been moved into the side vessel 42 a sufficient distance, i.e., a distance sufficient to remove the sheath 26 from between the prosthesis 24 and wall of the side vessel 42, the catheter 12 is then withdrawn back through the now expanded prosthesis 24. As shown in FIG. 9F, this movement, as represented by the arrow P back through the prosthesis 24, causes the sheath 26 to orient itself so as to follow along back through the prosthesis 24. The sheath 26, with reference to FIG. 9G, then trails along behind the balloon 22 portion of the catheter 12 as the catheter 12 is withdrawn in the direction shown by arrow P.

Figure 11:
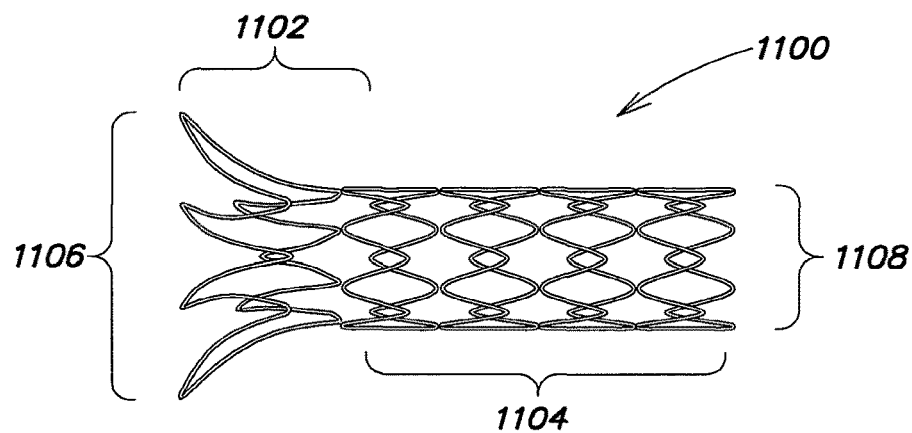
FIG. 11 is a schematic view of an another embodiment of an ostial protection device.

In another embodiment of the present disclosure, the prosthesis being delivered by the above-described delivery system is a self-expandable ostial protection device (OPD) as shown in FIG. 11. An OPD 1100 comprises a flared portion 1102 and a stem portion 1104. The OPD 1100, similar to the prosthesis 24 described above, may be comprised of a shape memory metal or super-elastic nickel titanium alloy such as Nitinol™. In alternative embodiments, the OPD 1100 has elastic properties due to design characteristics such as the use of spring-like connectors. In general, the OPD 1100 is designed to self-expand in the absence of a retaining element such as sheath 26. In an expanded state, the flared portion 1102 expands to a first diameter 1106 and the stem portion 1104 expands to a second diameter 1108 where the first diameter 1106 is greater than the second diameter 1108.

In one embodiment, the first diameter 1106 is at least 20% larger than the second diameter 1108 and, further, may be in a range of 20%-100% larger.

Figure 12:
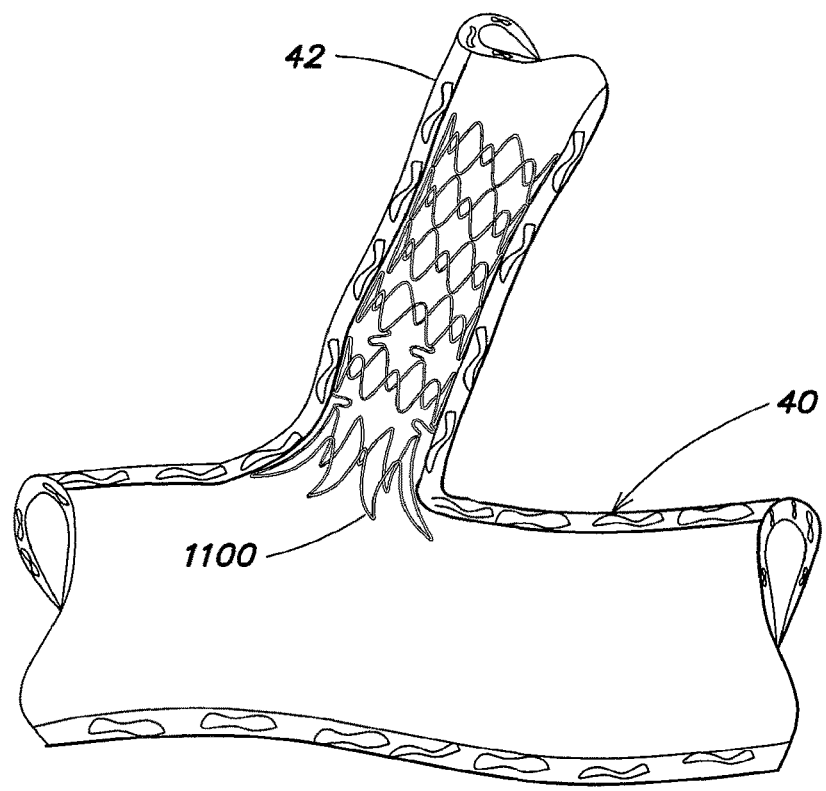
FIG. 12 is an illustration of the ostial protection device shown in FIG. 11 located in a side branch vessel.

As shown in FIG. 12, the OPD 1100 is meant to be positioned in the side branch 42 with the stem portion 1104 distally placed relative to the flared portion 1102 placed at the ostium to the main vessel 40.

The method of delivery of the OPD 1100 to the side branch 42 is similar to that which has been described above with respect to the other embodiments of the present disclosure. The OPD 1100 is positioned on the catheter 12 sandwiched between balloon 22 and sheath 26 in its compressed state. The OPD 1100 is oriented such that the flared portion 1102 is oriented toward the proximal end 14 of the catheter 12 while the stem portion 1104 is oriented toward the distal end 16 of the catheter 12. The sheath 26 is attached to the catheter at a location proximal to the balloon 22. Similar to the embodiments described above, the sheath 26 includes one or more openings 32 located at a distal end of the sheath to facilitate rupturing or tearing of the sheath 26.

Figure 13:
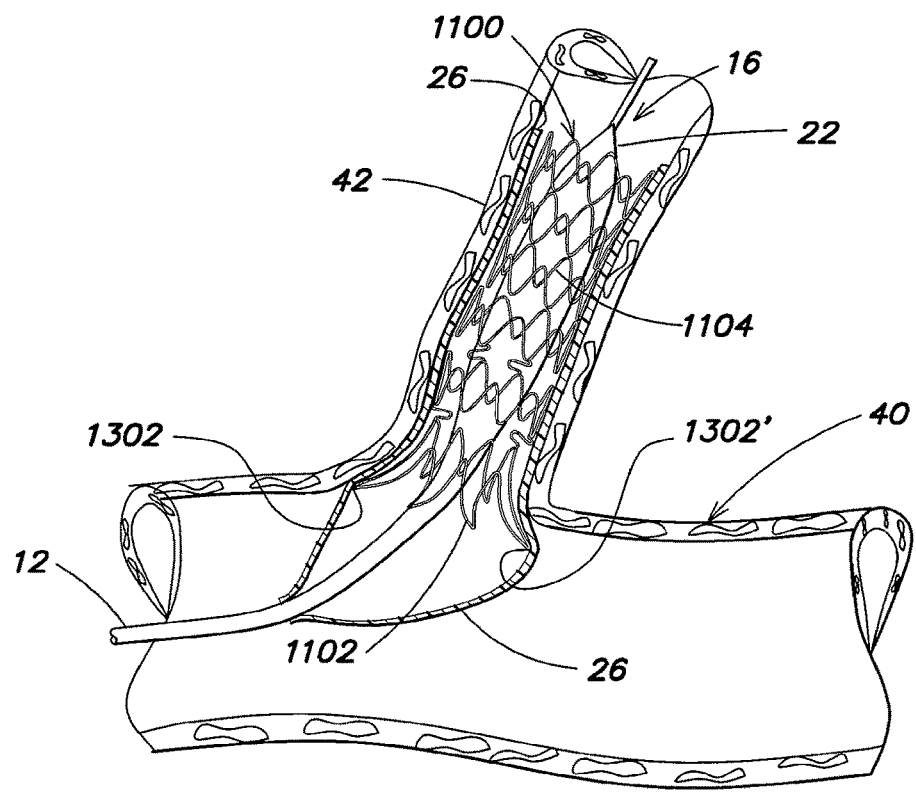
FIG. 13 is a cross-sectional illustration of the ostial protection device shown in FIG. 11 as being delivered to the side branch vessel.

The delivery of the OPD 1100 to the side branch 42 occurs in a manner similar to that described above with respect to the other embodiments of the present disclosure. The catheter 12 is advanced over a guidewire 20 until located at the desired position in the vasculature. Balloon 22 is then expanded, causing separation of sheath 26 originating at opening(s) 32 at a distal end of the sheath 26. This expansion of the balloon 22 causes release of the OPD 1100 from catheter 12. The OPD 1100 is deployed, placing at least a portion of sheath 26 between the stem portion 1104 and a wall of branch vessel 42, as shown in FIG. 13. Another portion of the ruptured sheath 26 is spread apart by the OPD flared portion 1102, allowing the stent to exit the sheath 26 and engage the vessel wall. As described above, balloon 22 is then deflated and the catheter 12, with sheath 26 attached thereto, is withdrawn from the branch vessel 42 without migration of the position of the OPD 1100.

It has been observed that the flared portion 1102 provides many points of contact around its periphery, points 1302, 1302' being representative in cross-section, to reduce the surface contact between the OPD 1100 and the sheath 26. This lifting of the ruptured sheath from an outer surface of the OPD 1100 provides a mechanical advantage to facilitate the removal of the sheath 26 from between the side branch vessel wall and the OPD 1100 without moving the OPD 1100 from its desired position. Withdrawal of the sheath 26 is thereby facilitated with accurate placement of the device.

Thus, in contrast to what may have been expected due to the results of the porcine experiments performed with known sheathed systems, a prosthesis such as the OPD 1100 of the present disclosure can be accurately placed in the vasculature as the movement of the OPD 1100 due to the withdrawal of the sheath 26 is minimized. In porcine experiments, OPDs were positioned with embodiments of the delivery system of the present disclosure within 1-2 mm of the desired location within a side branch vessel of the coronary arteries.

Figure 14:
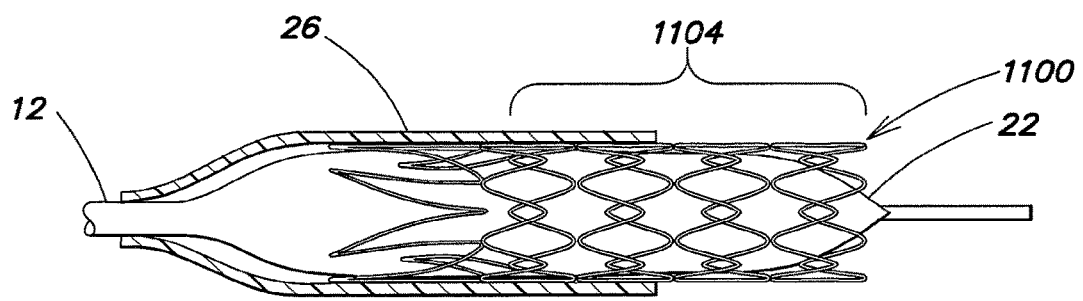
FIG. 14 is a transverse cross-sectional illustration of another embodiment of the delivery system.

Another embodiment of the present disclosure, with respect to the OPD 1100 is illustrated in FIG. 14. As shown in FIG. 14, the sheath 26 is connected to the catheter 12 at a location proximal to the balloon and proximal to the proximal ends of the sheath 26 and the OPD 1100. The sheath 26 extends from the proximal end of the OPD 1100 to enclose the OPD 1100 around the balloon 22. The sheath 26, however, does not extend all the way to the distal end of the OPD 1100. Rather, the sheath 26 covers a part of the stem portion 1104 sufficient to keep the entire stem portion 1104 from expanding. By covering enough of the stem portion 1104, the sheath 26 prevents that portion of the OPD from self-expanding prior to the inflation of the balloon when positioned at the desired location.

In the embodiment shown in FIG. 14, the distal end of the balloon 22 extends beyond the distal end of the sheath 26 to facilitate the tearing of the sheath 26. In an alternate embodiment, the distal end of the balloon 22 extends beyond the distal ends of the sheath 26 and the OPD 1100 or prosthesis 24. In yet another embodiment, the distal end of the balloon 22 extends beyond the distal end of the sheath 26 but not beyond the distal end of the prosthesis 24 or OPD 1100.

Similarly, at the proximal ends of the sheath 26, balloon 22 and prosthesis 24, 1100, the proximal end of the balloon may be located proximal to the proximal ends of the sheath 26, and prosthesis 24, 1100; located proximal to only the proximal end of the sheath 26; located proximal to only the proximal end of the prosthesis 24, 1100; or the proximal end of the balloon 22 may be distally located relative to the proximal ends of the sheath 26 and the prosthesis 24, 1100.

In alternate embodiments of that shown in FIG. 14, one or more openings 32 may be provided in accordance with that as shown in FIGS. 2A-2C.

In some embodiments, as shown in 15, a distal end portion of balloon 22 may include an enlarged diameter portion 50 that is distal to a distal end 25 of sheath 26. The enlarged diameter portion 50 may have an outer diameter D1 that is approximately the same as an outer diameter D2 of sheath 26 when prosthesis 24 is in a compressed state. For example, D1 may be equal to D2+/−5% when prosthesis 24 is in the compressed state and before sheath 26 has separated or torn along openings 32. Additionally, outer diameter D1 of enlarged diameter portion 50 may be the maximum outer diameter of balloon 22 when prosthesis 24 is in the compressed state. In embodiments, D1 is the maximum outer diameter of enlarged diameter portion 50 when prosthesis 24 is in the compressed state.

Figure 15:
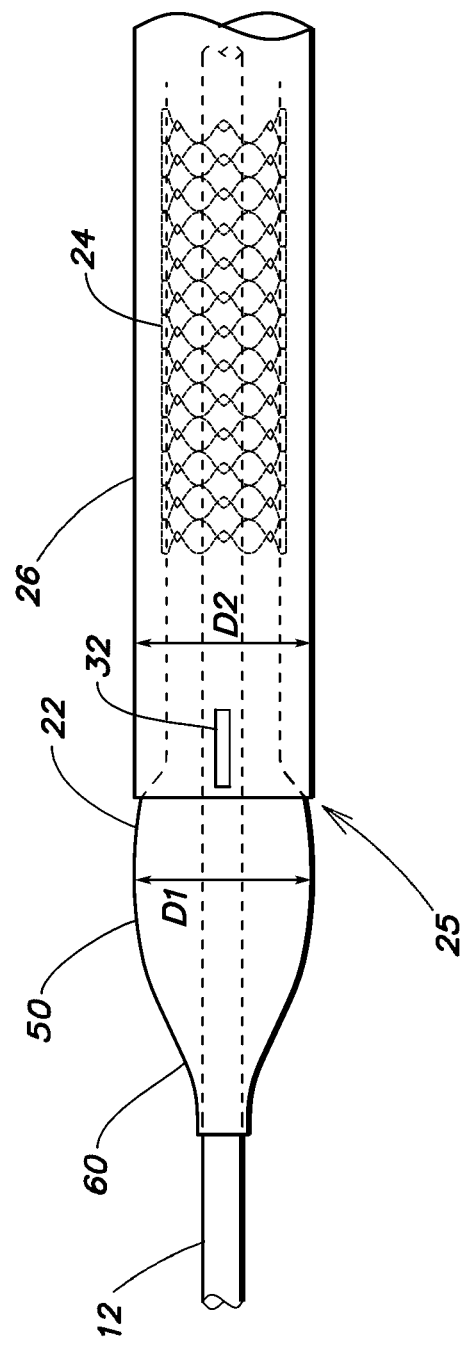
FIG. 15 is a longitudinal cross-sectional illustration of a delivery system in accordance with embodiments.

As shown in FIG. 15, distal end 60 of balloon 22, which is distal of enlarged diameter portion 50, may taper inward to an outer diameter of catheter 12 when prosthesis 24 is in the compressed state. Distal end 60 may vary in degree of tapering, and the tapering may include a smooth transition or an uneven transition to catheter 12. For example, the tapering may be intermittent and broken or may be one continuous transition. Additionally, enlarged diameter portion 50 may provide a smooth transition to the distal end 25 of the sheath 26 when prosthesis 24 is in the compressed state and before sheath 26 has separated or torn along openings 32.

As has been described above, the sheath 26 may comprise a biodegradable material or physiologically inert material. Further, the sheath may be coated or impregnated with a therapeutic agent for delivery to the vessel wall at which the prosthesis 24 is placed. A sheath 26 with a therapeutic agent therein may comprise either a biodegradable material or an inert material. Further, the prosthesis 24 may be a drug eluting device such as is known in the art.

Still further, the several openings 32 provided in the sheath 26 to facilitate the separation of the sheath 26 may vary in size and shape and position. The openings 32 may be provided in a pattern to cause the sheath 26 to break apart into a predetermined number of sections of a predetermined size.

Although the disclosure has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this disclosure are herein incorporated in their entirety by reference into the disclosure, to the same extent as if each individual publication, patent or patent application was specifically and individually indicated to be incorporated herein by reference. In addition, citation or identification of any reference in this application shall not be construed as an admission that such reference is available as prior art to the present disclosure.

The invention claimed is:

1. A delivery system comprising:
a catheter having a distal portion and a proximal portion;
a balloon disposed on the distal portion of the catheter;
a self-expanding prosthesis disposed on at least a portion of the balloon, the self-expanding prosthesis having a compressed state and an expanded state; and
a sheath coupling the self-expanding prosthesis to the balloon when the self-expanding prosthesis is in its compressed state, wherein:
the sheath includes an opening in a wall of the sheath that initiates rupturing of the sheath so that the self-expanding prosthesis may move from its compressed state to its expanded state,
a distal end portion of the balloon that is distal to a distal end of the sheath includes an enlarged diameter portion, the enlarged diameter portion having approximately a same outer diameter as an outer diameter of the sheath when the self-expanding prosthesis is in its compressed state, and the enlarged diameter portion being the maximum outer diameter of the balloon when the self-expanding prosthesis is in its compressed state,
the opening is at the distal end of the sheath, and
the enlarged diameter portion having approximately the same outer diameter as the outer diameter of the sheath when the self-expanding prosthesis is in its compressed state ensures that inflation of the balloon initiates rupturing of the sheath at the opening.

2. The delivery system according to claim 1, wherein a distal end of the balloon, distal of the enlarged diameter portion, tapers inward to an outer diameter of the catheter when the self-expanding prosthesis is in its compressed state.

3. The delivery system according to claim 1, wherein the enlarged diameter portion provides a smooth transition to the distal end of the sheath when the self-expanding prosthesis is in its compressed state.

4. The delivery system according to claim 1, wherein the opening in the wall of the sheath is a slit.

5. The delivery system according to claim 4, wherein a length of the slit extends for not more than 5% a length of the sheath.

6. The delivery system according to claim 4, wherein the slit includes a single slit on the sheath.

7. The delivery system according to claim 4, wherein the slit includes a plurality of linearly arranged slits.

8. The delivery system according to claim 4, wherein the slit includes a plurality of slits arranged circumferentially around a distal cross-section of the sheath.

9. The delivery system according to claim 4, wherein the slit extends along a grain longitudinal direction of the sheath.

10. The delivery system according to claim 1, wherein the delivery system has a first configuration for delivery to a target site within a vessel and a second configuration upon deployment of a prosthesis at the target site within the vessel, the enlarged diameter portion having approximately the same outer diameter as the outer diameter of the sheath when the delivery system is in the first configuration, and the enlarged diameter portion being the maximum outer diameter of the balloon when the delivery system is in the first configuration.

11. The delivery system according to claim 1, wherein the enlarged diameter portion of the balloon applies a radial force on the distal end of the sheath during inflation of the balloon.

\* \* \* \* \*